United States Patent [19]

Desmurs et al.

[11] Patent Number: 5,210,305
[45] Date of Patent: * May 11, 1993

[54] PROCESS FOR PREPARING N-ALKYLANILINES AND N-ALLYLANILINES

[75] Inventors: Jean Desmurs, Communay; Jean-Pierre Lecouve, Caluire, both of France

[73] Assignee: Rhone-Poulenc Chimie, Cedex, France

[*] Notice: The portion of the term of this patent subsequent to Feb. 23, 2010 has been disclaimed.

[21] Appl. No.: 674,315

[22] Filed: Mar. 25, 1991

Related U.S. Application Data

[63] Continuation of Ser. No. 386,433, Jul. 28, 1989, abandoned.

[30] Foreign Application Priority Data

Jul. 29, 1988 [FR] France ................. 88 10250

[51] Int. Cl.$^5$ ............................................. C07C 209/10
[52] U.S. Cl. ........................................ 564/404; 564/405
[58] Field of Search ............... 564/404, 405, 440, 441, 564/442

[56] References Cited

U.S. PATENT DOCUMENTS

| | | | |
|---|---|---|---|
| 2,286,678 | 6/1942 | Gubelmann | 564/404 |
| 3,668,254 | 6/1972 | D'Amico et al. | 564/434 |
| 3,819,708 | 6/1974 | Manning | 564/443 |
| 4,126,689 | 11/1978 | Sanzcuk et al. | 514/329 |
| 4,701,560 | 10/1987 | Regimbeau et al. | 564/404 |
| 4,956,496 | 9/1990 | Denis et al. | 564/404 |

FOREIGN PATENT DOCUMENTS

| | | | |
|---|---|---|---|
| 0019158 | 11/1980 | European Pat. Off. | 564/442 |
| 0205391 | 12/1986 | European Pat. Off. | 564/404 |
| 2305434 | 3/1976 | France . | |
| 1336484 | 4/1988 | U.S.S.R. | 564/404 |

Primary Examiner—Carolyn Elmore
Assistant Examiner—B. M. Burn
Attorney, Agent, or Firm—Finnegan, Henderson, Farabow, Garrett and Dunner

[57] ABSTRACT

The present invention relates to a process for the n-alkylation and n-allylation of anilines by bringing the aniline into contact with an alkylating or allylating agent in an organic solvent in a homogeneous liquid phase in the presence of an onium ion and a stoichiometric amount of a non-quaternizable base.

18 Claims, No Drawings

PROCESS FOR PREPARING N-ALKYLANILINES AND N-ALLYLANILINES

This application is a continuation, of application Ser. No. 07/386,433 filed Jul. 28, 1989, now abandoned.

BACKGROUND OF THE INVENTION

The present invention relates to a process for preparing N-alkylanilines and N-allylanilines. It relates more specifically to the preparation of N-allylanilines, and still more specifically to the preparation of N-monoallylanilines.

The preparation of N-monoallylanilines is especially important. For example, in the case of trifluoromethylaniline, the monoallyl derivative obtained is an important intermediate in the synthesis of a herbicide as described in French Patent 2,305,434. According to this patent, to prepare the desired herbicide, 1-[N-(meta-trifluoromethylphenyl)]-3-chloro-4-chloromethyl-2-pyrolidone, it is necessary to start with a trifluoromethylaniline and protect one of the hydrogen atoms by adding an acetyl group before performing the allylation to create a monoallyltrifluoromethylaniline. The object of these extra steps is to avoid the formation of diallyl by-products which are unusable.

There has been a long-felt need in the industry to find a means of preparing a monoallyltrifluoromethylaniline directly in a single stage, instead of the three stages as described in French Patent 2,305,434, with good yields calculated with respect to the starting material employed, meta-trifluoromethylaniline, which is a very expensive compound which the industry has no wish to waste.

U.S. Pat. No. 4,701,560 attempted to solve this problem with a process for the allylation of meta-trifluoromethylaniline in a two-phase, water/organic solvent medium in the presence of an inorganic base chosen from carbonates or sodium hydroxide and in the presence of catalytic amounts of a quaternizable tertiary amine. To reduce the amount of undesirable diallyl by-products, it is necessary to limit the degree of conversion of the meta-trifluoromethylaniline, and hence to work in the presence of a deficiency of allyl halide; it is specified in this text that the ratio of meta-trifluoromethylaniline to the allyl halide is preferably approximately 2:1. Thus, the starting material is used in a non-stoichiometric amount and the yields of N-monoallyltrifluoromethylaniline calculated with respect to the meta-trifluoromethylaniline introduced do not exceed 40%. This is insufficient for an economically profitable and commercially successful process.

Allylation reactions with anilines other than meta-trifluoromethylaniline are also described. For example, U.S. Pat. No. 2,286,678 describes the allylation of para-hydroxyaniline in a medium consisting of an alcohol and in the presence of carbonate as a neutralizing agent.

The stated yields of N-monoallylhydroxyaniline do not exceed those of the previous patent. Also, this process results in the formation of a significant amount of diallyl derivatives which are undesirable biproducts. Therefore, this technique is also not applicable to the preparation of a N-monoallylated product in a single stage with good yield and little production of unwanted diallyl derivatives.

A process which consists of allylating 4-aminodiphenylamine with 2,3-dichloropropene in the presence of triethylamine is described in U.S. Pat. No. 3,668,254. The stated yields, as in the previous two processes, do not exceed 40%. In addition, triethylamine is used in a more than stoichiometric amount relative to the allyl halide. From an economic standpoint, this technique is disadvantageous on two accounts, the yields are low and the cost of the starting materials employed is too high.

U.S. Pat. No. 3,819,708 describes the alkylation of para-phenylenediamines in various solvents, in the presence of a tertiary amine such as triethylamine or an inorganic base as a neutralizing agent for the hydracid formed. The alkylating agents which are described are much less reactive than allyl halides, and the problem of dialkylation is hence much smaller. The selectivity, that is to say the yield of monoalkyl product relative to the dialkyl derivatives, is never described.

Despite the existence of an abundant literature describing the alkylation or allylation of various anilines, no process has ever been developed which solves the problems of preparing a N-monoalkylaniline or N-monoallylaniline that produces a good yield and very little unusable dialkyl or diallyl by-products. In other words, a process where there is a good degree of conversion of the starting aniline and good selectivity for the aniline monosubstituted on the nitrogen instead of the aniline disubstituted on the nitrogen.

It is an object of the present invention to provide a new process for producing N-alkylation and N-allylation of an aniline which avoids the disadvantages of previously-known processes. The new process will enable someone skilled in the art to produce high yields of N-monoalkylated or N-monoallylated anilines with very low formation of unusable dialkyl or diallyl derivatives.

Additional objects and advantages of the invention will be set forth in the description which follows, and in part will be apparent from the description, or may be learned by practice of the invention. The objects and advantages of the invention may be realized and obtained by means of instrumentalities and combinations particularly pointed out in the appended claims.

SUMMARY OF THE INVENTION

To achieve the foregoing objects, and in accordance with the purposes of the invention as embodied and broadly described herein, there is provided a process for the N-alkylation and N-allylation of an aniline, wherein the aniline and an alkylating or allylating agent are brought into contact in an organic solvent in a homogeneous liquid phase in the presence of a catalytic amount of an onium ion and a stoichiometric amount of a non-quaternizable base.

The alkylating or allylating agent is chosen from alkyl halides or sulfates in which the alkyl chain can contain unsaturated bonds, can be linear or branched and can, in addition, contain substituents chosen from halo, aryl, aralkyl, haloaryl and nitroaryl radicals.

Among halides, it is preferable to use chlorides and bromides, and more specifically chlorides because they are less expensive.

Among alkyl and allyl halides, the present invention relates more specifically to allyl halides, since they are agents of low reactivity with respect to allylation, especially the chlorides.

Some of the alkylating and allylating agents which may be used are:
allyl chloride
allyl bromide benzyl chloride
benzyl bromide
isoproply bromide
crotyl chloride
1-chloro-2-butene The process of the present invention may be applied to any anilines. Anilines of low basicity, a pKa of less than 4.5, are particularly preferred. Nevertheless, the process of the invention possesses an advantage for the alkylation or allylation of all anilines.

In the case of reactive anilines, the use of onium ions enables the reaction time or the reaction temperature to be reduced considerably. The reaction time and the reaction temperature are often linked in the process.

The preferred anilines, those possessing a pKa of less than 4.5, are represented by the following formula (I):

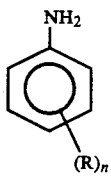
(I)

in which
R denotes:
  a halogen
  a group - A $C_n X_{2n+1}$ where X denotes halogen, A a covalent bond or an oxygen or sulfur atom,
  a nitro group
n is equal to 0, 1 or 2.

Some of the preferred anilines of formula (I) which may be used are:
aniline
chloroanilines
fluoroanilines
nitroanilines
trihalomethylanilines
trihalomethoxyanilines
trihalomethylthioanilines The onium ions referred to in the present invention are cations where the covalency of a specific element in an uncharged compound is increased by coordination with hydrocarbon residues. The resultant ion is called an "onium ion."

The onium ions used in the process according to the invention are those derived, in particular, from nitrogen, phosphorus, arsenic, sulfur, selenium, oxygen, carbon or iodine. The onium ions derived from nitrogen, phosphorus or arsenic will be tetracoordinated, the onium ions derived from sulfur, selenium, oxygen, carbon or S=O will be tricoordinated.

The hydrocarbon residues coordinated to these different components are alkyl, alkenyl, aryl, cycloalkyl or arylalkyl radicals, optionally substituted, since it is possible for two coordinated hydrocarbon residues to form together a single divalent radical.

Among onium ions which can be used in the present process, those corresponding to one of the following general formulae are especially suitable:

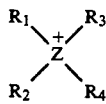
(II)

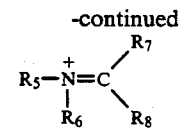
(III)

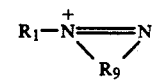
(IIIa)

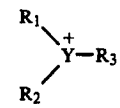
(IV)

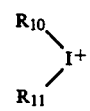
(V)

in which:
Z denotes N, P or As;
Y denotes S, O, Se, S=O, or C;
$R_1$, $R_2$, $R_3$, and $R_4$, which may be identical or different denote:
  a linear or branched alkyl radical having 1 to 16 carbon atoms and optionally substituted with one or more phenyl, hydroxyl, halo, nitro, alkoxy or alkoxycarbonyl groups or atoms, the alkoxy groups having 1 to 4 carbon atoms;
  a linear or branched alkenyl radical having 2 to 12 carbon atoms;
  an aryl radical having 6 to 10 carbon atoms, optionally substituted with one or more alkyl groups having 1 to 4 carbon atoms, alkoxy or alkoxycarbonyl groups, the alkoxy radical having 1 to 4 carbon atoms, or halogen atoms;
  two of the said radicals $R_1$ to $R_4$ being capable of forming together a linear or branched alkylene, alkenylene or alkadienylene radical having from 3 to 6 carbon atoms;
$R_5$, $R_6$, $R_7$ and $R_8$ are identical or different and denote:
  a linear or branched alkyl radical containing from 1 to 4 carbon atoms;
  the radicals $R_7$ and $R_8$ being capable of forming together an alkylene radical containing from 3 to 6 carbon atoms;
  the radicals $R_6$ and $R_7$ or $R_6$ and $R_8$ being capable of forming together an alkylene, alkenylene or alkadienylene radical containing 4 carbon atoms and forming with the nitrogen atom a nitrogenous heterocycle;
$R_9$ denotes a divalent radical forming, with the 2 nitrogen atoms, a ring having 4 to 6 atoms capable of containing one or more nitrogen, sulfur and/or oxygen atoms, the said ring being capable of being substituted with one or more radical such as $R_1$;
$R_{10}$ and $R_{11}$ denote identical or different aryl radicals.

Examples of onium ions which correspond to the formula (II), are:
tetramethylammonium,
triethylmethylammonium,
tributylmethylammonium,
trimethylpropylammonium,
tetraethylammonium,
tetrabutylammonium,
dodecyltrimethylammonium,
methyltrioctylammonium, heptyltributylammonium,
tetrapropylammonium,
tetrapentylammonium,
tetrahexylammonium,
tetraheptylammonium,
tetraoctylammonium,
tetradecylammonium,
butyltripropylammonium,
methyltributylammonium,
pentyltributylammonium,
methyldiethylpropylammonium,
ethyldimethylpropylammonium,
tetradodecylammonium,
tetraoctadecylammonium,
hexadecyltrimethylammonium,
benzyltrimethylammonium,
benzyldimethylpropylammonium,
benzyldimethyloctylammonium,
benzyltributylammonium,
benzyltriethylammonium,
phenyltrimethylammonium,
benzyldimethyltetradecylammonium,
benzyldimethylhexadecylammonium,
dimethyldiphenylammonium,
methyltriphenylammonium,
(2-butenyl)triethylammonium,
(N,N-dimethyl)tetramethyleneammonium,
(N,N-diethyl)tetramethyleneammonium,
tetramethylphosphonium,
tetrabutylphosphonium,
ethyltrimethylphosphonium,
trimethylpentylphosphonium,
octyltrimethylphosphonium,
dodecyltrimethylphosphonium,
trimethylphenylphosponium,
diethyldiphenylphosponium,
dicyclohexyldimethylphosphonium,
dimethyldiphenylphosphonium,
cyclohexyltrimethylphosphonium,
triethylmethylphosphonium,
methyltri(isopropyl)phosphonium,
methyltri(n-propyl)phosphonium,
methyltri(n-butyl)phosphonium,
methyltris(2-methylpropyl)phosphonium,
methyltricyclohexylphosphonium,
methyltriphenylphosphonium,
methyltribenzylphosphonium,
methyltris(4-methylphenyl)phosphonium,
methyltrixylylphosphonium,
diethylmethylphenylphosphonium,
dibenzylmethylphenylphosphonium,
ethyltriphenylphosphonium,
tetraethylphosphonium,
ethyltri(n-propyl)phosphonium,
triethylpentylphosphonium,
hexadecyltributylphosphonium,
ethyltriphenylphosphonium,
n-butyltri(n-propyl)phosphonium,
butyltriphenylphosphonium,
benzyltriphenylphosphonium,
(b-phenylethyl)dimethylphenylphosphonium,
tetraphenylphosphonium,
triphenyl(4-methylphenyl)phosphonium,
tetrakis(hydroxymethyl)phosphonium,
tetraphenylarsonium.

Examples of onium ions which correspond to the formulae (III) and (IIIa) are:
N-methylpyridinium,
N-ethylpyridinium,
N-hexadecylpyridinium,
N-methylpicolinium,
1,2,4-triphenyltriazolium.

Examples of organic onium ions which correspond to the formula (IV) are:
trimethylsulfonium,
triethylsulfonium,
triphenylsulfonium,
trimethylsulfoxonium,
triphenylcarbenium,
triethyloxonium.

Examples of onium ions which correspond to the formula (V) are:
diphenyliodonium,
4,4'-dimethoxydiphenyliodonium (or the compounds described in J. Am. Chem. Soc. 1958, 81, 342),
diphenyliodonium-2-carboxylate (Japanese patent application JP 63 005040).

In the class of onium ions, it is preferable to use onium ions which have a molecular weight of between 150 and 400, and more preferably between 200 and 300. Among these onium ions, ammonium ions in which the four alkyl groups are similar and possess four to five carbon atoms are more specifically preferred.

The onium ion may be combined with an anion. Some of which are halides, hydroxyls, hydrogen sulfates, trifluoromethanesulfonates and hexachloroantimonates.

The onium compound can be soluble in the reaction medium, in which case the reaction will take place in a homogeneous medium, or insoluble in solid form, in which case the reaction will take place in a two-phase, solid/liquid medium. The onium compound can also be supported on an inorganic or polymeric resin.

Examples of "supported" onium compounds are:
tetrabutylammonium fluoride on silica gel
tributylammonium chloride on polymer marketed, for example, by the FLUKA company
methyltributylphosphonium chloride linked to polystryrene marketed, for example, by the FLUKA company
benzyltrimethylammonium bromide on polymer.

When the onium compound is supported on an inorganic or polymeric resin, the reaction will take place in a two-phase, solid/liquid medium.

The base used in the process of the invention serves to neutralize the hydracid liberated during the alkylation or allylation. Inorganic bases such as carbonates or sodium hydroxide, or organic bases such as sodium acetate, or non-quaternizable tertiary amines may be used.

Non-quaternizable tertiary amines are defined as all tertiary amines possessing at least one branched alkyl chain, preferably at least two branched alkyl chains.

Examples of these amines, are:
diisopropylallylamine
diisopropylethylamine
trisopropylamine.

Among the group of the bases mentioned, it is more preferable to use diisopropylethylamine.

The onium ion may be introduced completely synthesized in the reaction medium, or be prepared "in situ". In the latter case, the catalytic amount of a quaternizable tertiary amine which, in the presence of the alkyl or allyl halide, will give the desired ammonium compound is used. This amine is preferably triethylamine.

The solvent forming the reaction medium must solubilize the aniline and the alkyl or allyl halide; the onium compound or the base, which can be solid, are not always solubilized by the reaction medium, but it is nevertheless preferable that both the compound and base are soluble in the reaction medium.

Examples of suitable solvents are:

aliphatic hydrocarbons such as
  hexane
  cyclohexane
  heptane
  octane
aromatic hydrocarbons such as
  toluene
  xylene
halogenated hydrocarbons such as
  chloroform
  methylene chloride
  chlorobenzene
  carbontetrachloride
  dichloroethane
alcohols such as
  ethanol
  isopropanol
  butanol
  octanol
polar aprotic solvents such as
  N,N-dimethylformamide
  acetonitrile
  N-methylpyrrolidone
non-quaternizable tertiary amines such as
  diisopropylethylamine.

Among the group of solvents mentioned, it is more preferable to use heptane or diisopropylethylamine.

For improved implementation of the invention, it is preferable to use an approximately stoichiometric amount of alkyl or allyl halide relative to the aniline. When the base is used to form the onium ion "in situ", the amount of alkyl or allyl halide will exceed the stoichiometric amount relative to the aniline.

The onium ion is used in a catalytic amount which is a mole ratio of between 0.025 and 0.2 relative to the aniline.

The preferred reaction temperature is between 0° C. and 150° C., and more preferably between 25° C. and 80° C. The temperature will vary depending on the reactants used in the process, especially depending on the pKa of the aniline and the nature of the halide.

The reaction pressure is preferably atmospheric pressure.

The reaction time will vary between one and a few hours.

These and other features and advantages of the present invention will be more apparent from the following description of the preferred embodiments, which are not to be regarded as limiting the invention.

EXAMPLES 1 TO 12

A 30-ml reactor is charged with:
0.64 of m-trifluoromethylaniline (4 mmol)
0.3 of allyl chloride (4 mmol)
2 ml of solvent (Examples 1-12 in Table 1 show the reaction yield with 12 different solvents)
0.51 g of diisopropylethylamine (4 mmol) and, where appropriate, allyltriethylammonium bromide (0.4 mmol). The reaction mixture is heated for 3 h 30 min to 80° C. At the end of the reaction, after cooling, 5 ml of N sodium hydroxide are added. The organic products are extracted with 3×10 ml of isopropyl ether.

The combined organic phase is diluted to 50 ml in a volumetric flask and assayed by GC.

In the following tables, the degree of conversion (DC) is calculated as follows:

$$DC = \frac{\text{number of moles of aniline converted}}{\text{number of moles of aniline introduced}} \%$$

$$YD = \frac{\text{number of moles of product formed}}{\text{number of moles of aniline converted}} \%$$

$$\text{Selectivity} = \frac{\text{amount of N-alkyl or N-allyl formed}}{\text{amount of N-alkyl or n-allyl formed + amount of dialkyl or diallyl formed}}$$

TABLE 1

The following table illustrates the results of the process in Examples 1 to 12 with the addition of onium ion and control experiments, labelled C-1, C-2, etc., in which the onium ion is not added.

| Exp. | Onium | Solvent | ε | DC mTFMA | YD N-allyl | YD di-allyl | Accounted for |
|---|---|---|---|---|---|---|---|
| 1 | yes | Heptane | 1.8 | 77% | 82% | 6.5% | 96% |
| C 1 | no | | | 7.5% | 100% | 0% | 100% |
| 2 | yes | CCl₄ | 2.2 | 25% | 100% | trace | 100% |
| C 2 | no | | | 0% | 0% | 0% | 100% |
| 3 | yes | Toluene | 2.4 | 67.5% | 77% | 4.2% | 87.2% |
| C 3 | no | | | 0% | 0% | 0% | 100% |
| 4 | yes | Isopropyl ether | 3.5 | 12.5% | 100% | trace | 100% |
| C 4 | no | | | 3.5% | 71% | 28% | 100% |
| 5 | yes | CHCl₃ | 5.1 | 18% | 100% | trace | 97.5% |
| C 5 | no | | | 0% | 0% | 0% | 100% |
| 6 | yes | ClCH₂—CH₂Cl | 10.5 | 30% | 94% | 6% | 100% |
| C 6 | no | | | 2.5% | 75% | 24% | 99% |
| 7 | yes | 1-octanol | | 47% | 66.4% | 33.6% | 104% |
| C 7 | no | | | 18.4% | 100% | trace | 95% |
| 8 | yes | 1-butanol | 18 | 66% | 95% | 7.6% | 106% |
| C 8 | no | | | 25% | 40% | trace | 87.5% |
| 9 | yes | Ethanol | 24.3 | 40% | 75% | 3% | 81% |
| C 9 | no | | | 15% | 100% | 0% | 100% |
| 10 | yes | DMF | 36.7 | 58.7% | 70% | 5.1% | 85.7% |
| C 10 | no | | | 11% | 100% | 0% | 100% |
| 11 | yes | CH₃CN | 37.5 | 12.5% | 100% | 0% | 88% |
| C 11 | no | | | 2.5% | 100% | 0% | 87% |
| 12 | yes | Diiso-propyl- | | 62.6% | 91.12% | 7.94% | 99.3% |
| C 12 | no | | | 5% | 100% | 0% | 100% |

TABLE 1-continued

The following table illustrates the results of the process in Examples 1 to 12 with the addition of onium ion and control experiments, labelled C-1, C-2, etc., in which the onium ion is not added.

| Exp. | Onium | Solvent | ε | DC mTFMA | YD N-allyl | YD di-allyl | Accounted for |
|------|-------|---------|---|----------|------------|-------------|---------------|
|      |       | ethylamine |   |          |            |             |               |

EXAMPLES 13 AND 14

Allylation with Onium Salts

The procedure is as in Example 1, charging:
0.64 g of trifluoromethylaniline (4 mmol)
2 ml of heptane
4 mmol of onium chloride The reaction mixtures are heated for 5 hours at 75°.

TABLE 2

The following table illustrates control experiments in which aniline is not added.

| Exp. | Conditions | Onium* | DC mTFMA | YD N-allyl | YD di-allyl | Accounted for |
|------|-----------|--------|----------|------------|-------------|---------------|
| C 13 | 75° C. - 5 h | ⁀N Et₃Cl | 0 | 0 | 0 | 100 |
| C 14 | 75° C. - 5 h | ⁀Pφ₃Cl | 0 | 0 | 0 | 100 |

*⁀ is the allyl group $CH_2=CH-CH_2-$;

⁀N Et₃Cl is allyl triethyl ammonium chloride,

⁀Pφ₃Cl is allyl triphenylphosphonium chloride.

Onium halides are not allylating under the working conditions employed.

EXAMPLES 13 TO 17

Influence of the Amount of Onium Ion

The procedure as in Example 1 is employed, charging:
0.64 g of m-trifluoromethylaniline (4 mmol)
2 ml of heptane
0.3 g of allyl chloride (4 mmol)
0.5 g of diisopropylethylamine (4 mmol)
and amounts of allyltriethylammonium bromide ranging from 0 mmol to 4 mmol. The reaction is allowed to proceed for 4 hours.

TABLE 3

| Exp. | ⁀NEt₃Br | DC mTFMA | YD N-allyl | YD di-allyl | Accounted for | Selectivity |
|------|---------|----------|------------|-------------|---------------|-------------|
| C 15 |         | 7.5%     | 100%       | 0%          | 100%          | 100%        |
| 13   | 0.1 mmol | 30%     | 90.2%      | 9.7%        | 100%          | 90.2%       |
| 14   | 0.4 mmol | 59%     | 95.2%      | 4.8%        | 100%          | 95.2%       |
| 15   | 0.8 mmol | 79%     | 92%        | 8%          | 102%          | 92%         |
| 16   | 1.6 mmol | 70.4%   | 83.8%      | 6%          | 105%          | 94%         |
| 17   | 4 mmol   | 86.6%   | 87.1%      | 13%         | 100%          | 87.1%       |

Experiment C-15 illustrates a control experiment where the onium is not added.

EXAMPLES 18 TO 30

Influence of the Structure of the Ammonium Compound

The procedure in Example 1 is employed, charging:
0.64 of m-trifluoromethylaniline (4 mmol)
2 ml of heptane
0.3 g of allyl chloride (4 mmol)
0.5 g of diisopropylethylamine (4 mmol)
and 0.4 mmol of an ammonium compound. The reaction is performed at 80° for 4 hours.

TABLE 4

| Exp. | Onium | MW | DC mTFMA | YD N-allyl | YD di-allyl | Accounted for | Selectivity |
|------|-------|-----|----------|------------|-------------|---------------|-------------|
| 18   | NH₄CL* | 53.5 | 10% | 100% | trace | 100% | 100% |
| 19   | NMe₄Cl* | 109.6 | 17% | 66% | 2% | 98% | 97% |

TABLE 4-continued

| Exp. | Onium | MW | DC mTFMA | YD N-allyl | YD di-allyl | Ac-counted for | Selec-tivity |
|---|---|---|---|---|---|---|---|
| 20 | (allyl)$_2$—NMe$_2$—Cl* | 161 | 47.5% | 94.7% | trace | 100% | 100% |
| 21 | Et$_4$NCl | 165.5 | 44.7% | 96.7% | 3.3% | 106% | 96.7% |
| 22 | ONMe$_3$—Cl | 171.6 | 75% | 83.3% | 4% | 92% | 96.4% |
| 23 | allyl-NEt$_3$—Cl | 177.5 | 58% | 91.1% | 8.9% | 96% | 91.1% |
| 24 | OCH$_2$—NEt$_3$Cl | 227.8 | 62% | 92% | 4% | 98% | 96% |
| 25 | MeNBu$_3$—Cl | 235.5 | 72.5% | 81% | 5.8% | 90.5% | 93.2% |
| 26 | Bu$_4$NCl | 277 | 70% | 93% | 5.3% | 98.3% | 94.5% |
| 27 | OCH$_2$—NBu$_3$Cl | 312.5 | 72% | 93% | 7% | 100% | 93% |
| 28 | B—N(pyridinium)—C$_{16}$H$_{33}$Cl | 358 | 57% | 30% | 0.8% | 60% | 97% |
| 29 | MeN—(C$_8$H$_{17}$)$_3$—Cl | 404 | 42% | 94% | 1.7% | 90% | 97% |
| 30 | OCH$_2$—NMe$_2$—C$_{16}$H$_{33}$ | 414 | 40% | 98% | trace | 100% | 100% |

*Ammonium compounds insoluble in the reaction medium.

EXAMPLES 31 TO 36

Influence of the Length of Chain of the Ammonium Compound

The procedure in Example 1 is employed, charging:
0.64 g of m-trifluoromethylaniline (4 mmol)
2 ml of heptane
0.3 g of allyl chloride (4 mmol)
0.5 of diisopropylethylamine (4 mmol)
and 0.4 mmol of an ammonium chloride. The reaction is performed at 80° for 4 hours.

TABLE 5

| Exp. | Onium | MW | DC mTFMA | YD N-allyl | YD di-allyl | Ac-counted for | Selec-tivity |
|---|---|---|---|---|---|---|---|
| 31 | NH$_4$Cl | 53.5 | 10% | 100% | trace | 100% | 100% |
| 32 | NMe$_4$Cl | 109.6 | 17% | 66% | 2% | 98% | 97% |
| 33 | NEt$_4$Cl | 165.5 | 44.7% | 96.7% | 3.3% | 106% | 96.7% |
| 34 | NBu$_4$Cl | 277 | 70% | 93% | 5.3% | 98.3% | 94.5% |
| 35 | N(C$_5$H$_{11}$)$_4$Cl | 333.5 | 60% | 83.3% | 4.1% | 92.5% | 95.3% |
| 36 | N(C$_6$H$_{13}$)$_4$Cl | 389.5 | 52.5% | 80% | 4.7% | 92% | 94.5% |

EXAMPLES 37 TO 49

Influence of the Anion of the Onium Compound

The procedure in Example 1 is employed, charging:
0.64 g of m-trifluoromethylaniline (4 mmol)
2 ml of heptane
0.3 g of allyl chloride (4 mmol)
0.5 g of diisopropylethylamine (4 mmol)
and 0.4 mmol of an onium salt. The reaction is performed at 80° for 4 hours.

TABLE 6

Cation:  Net$_3$ (allyl triethylammonium)

| Exp. | Counter-ion | DC mTFMA | YD N-allyl | YD di-allyl | Ac-counted for | Selec-tivity |
|---|---|---|---|---|---|---|
| 37 | Cl$^-$ | 58.3% | 91.1% | 8.9% | 100% | 91.1% |
| 38 | Br$^-$ | 70% | 78.6% | 3.5% | 87.5% | 95.7% |

TABLE 7

Cation: 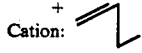 Pφ₃ (allyl triphenylphosphonium)

| Exp. | Counter-ion | DC mTFMA | YD N-allyl | YD di-allyl | Ac-counted for | Selec-tivity |
|---|---|---|---|---|---|---|
| 39 | Cl⁻ | 53% | 98% | 2% | 100% | 98% |
| 40 | Br⁻ | 75% | 93.3% | 6.6% | 100% | 93.3% |

TABLE 8

Cation: Et₄N⁺ (tetraethylammonium)

| Exp. | Counter-ion | DC mTFMA | YD N-allyl | YD di-allyl | Ac-counted for | Selec-tivity |
|---|---|---|---|---|---|---|
| 41 | Cl⁻ | 44% | 96.7% | 3.3% | 106% | 85.6% |
| 42 | Br⁻ | 77.5% | 93.5% | 6.4% | 100% | 93.5% |

TABLE 9

Cation: Bu₄N⁺ (tetrabutylammonium)

| Exp. | Counter-ion | DC mTFMA | YD N-allyl | YD di-allyl | Ac-counted for | Selec-tivity |
|---|---|---|---|---|---|---|
| 43 | OH⁻ | 42% | 98% | trace | 100% | 100% |
| 44 | ClO₄⁻ | 45% | 99% | trace | 100% | 100% |
| 45 | HSO₄⁻ | 54% | 95.2% | 4.8% | 100.5% | 95.2% |
| 46 | CF₃SO₃⁻ | 46% | 88.8% | 3.3% | 96% | 96.3% |
| 47 | Br₃⁻ | 68.5% | 92% | 8% | 100% | 92% |
| 48 | Cl⁻ | 70% | 93% | 5.3% | 100% | 94.5% |
| 49 | Br⁻ | 67.9% | 93% | 7% | 100% | 93% |

EXAMPLES 50 TO 54

Influence of the Nature of the Onium Ion or Cation Radicals

The procedure is as in Example 1, charging:
0.64 of m-trifluoromethylaniline (4 mmol)
0.3 g of allyl chloride (4 mmol)
2 ml of heptane
0.51 g of diisopropylethylamine (4 mmol)
and 0.4 mmol of an onium compound. The reaction is performed at 80° for 4 hours.

TABLE 10

| Exp. | Onium | DC mTFMA | YD N-allyl | YD N,N-diallyl |
|---|---|---|---|---|
| 50 | (O)₃— | 43.6% | 85.7% | 9.3% |
| 51 | (O)₄PCl | 50% | 95.8% | 4.1% |
| 52 | (O)₂ICl | 43.6% | 80% | 3.5% |
| 53 | (O)₄AsCl | 61.4% | 91.6% | 5.4% |
| 54 | (BrO)₃—N SbCl₆ | 63.7% | 78.4% | 4.7% |
|    | CSbCl₅ |    |    |    |

EXAMPLES 55 TO 58

Influence of Supported Onium Compounds

The procedure is as in Example 1, charging:
0.64 of m-trifluoromethylaniline (4 mmol)
0.3 g of allyl chloride (4 mmol)
2 ml of heptane
0.51 g of diisopropylethylamine (4 mmol)
and an amount of supported onium compound. The reaction is performed at 80° for four hours.

TABLE 11

| Exp. | Onium | DC mTMFA | YD N-allyl | YD di-allyl | Ac-counted for | Selec-tivity |
|---|---|---|---|---|---|---|
| 55 | 0.45 mmol of Cl Ⓟ-CH₂—NBu₃Cl | 57.7% | 87.5% | 6% | 96% | 90.5% |
| 56 | 0.39 mmol of Cl P—CH₂—PBu₃Cl | 72.6% | 92.4% | 6% | 99% | 93% |
| 57 | 0.67 mmol of Br Ⓟ-C₆H₄—CH₂N—(CH₃)₃Br | 82% | 79% | 7.8% | 89% | 91% |
| 58 | Bu₄NF on silica gel 0.83 mmol of F | 77% | 80.5% | 7.6% | 90.7% | 91.3% |

Ⓟ is a polymer.

EXAMPLES 59 TO 65

Influence of the Base

The procedure is as in Example 1, charging:
0.64 g of m-trifluoromethylamine (4 mmol)
0.6 g of allyl chloride (8 mmol)
2 ml of heptane
4 mmol of a base
and, where appropriate, 0.4 or 4 mmol of allyltriethylammonium bromide. The reaction is performed at 75° for three hours.

TABLE 12

| Exp. | Onium | Base | DC mTFMA | YD N-allyl | YD N,N-diallyl |
|---|---|---|---|---|---|
| C 59 | no | 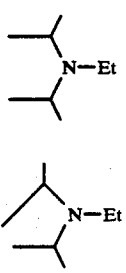 N—Et | 4.4% | 100% |  |
| 59 | yes (4 mmol) | N—Et | 97% | 54% | 4.0 |
| C 60 | no | AcONa | 4.8 | 0 | 0 |
| 60 | yes | AcONa | 66.9 | 75.4 | 1.2 |

TABLE 12-continued

| Exp. | Onium | Base | DC mTFMA | YD N-allyl | YD N,N-diallyl |
|------|-------|------|----------|------------|----------------|
|      | (0.4 mmol) |  |  |  |  |
| 61   | yes   | AcONa | 96.7 | 49.9 | 50.2 |
|      | (4 mmol) |  |  |  |  |

A second series of experiments was performed at 75° in the course of 2 h 30 min, charging:
0.64 g of m-trifluoromethylanilane
0.3 g of allyl chloride (4 mmol)
2 ml of heptane
5 mmol of base
0.4 mmol of allyltriethylammonium bromide

TABLE 13

| Exp. | Solvent | Temp/time | Base | DC mTFMA | YD N-allyl | YD N,N-diallyl |
|------|---------|-----------|------|----------|------------|----------------|
| 62 | Heptane | 75°-2 h 30 | NaOH | 77.6 | 77.8 | 10 |
| 63 | Heptane | 75°-2 h 30 | $K_2CO_3$ | 49.6 | 81.6 | 6.4 |
| 64 | Heptane | 75°-2 h 30 | $Na_2CO_3$ | 50.5 | 76.6 | 6.2 |
| 65 | Heptane | 75°-2 h 30 | 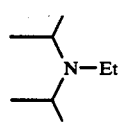 | 88.3 | 34.6 | 6.2 |

EXAMPLE 66

Experiment on Recycling the Supported Ammonium Compound 1st Operation

A reactor is charged with:
0.64 g of m-trifluoromethylaniline (4 mmol)
0.3 g of allyl chloride (4 mmol)
2 ml of diisopropylethylamine and an amount of P—O—$CH_2$—N $Me_3Br$ corresponding to 0.4 mmol of $Br^+$.

The reaction is performed at 80° for 4 hours. At the end of the reaction, the resin is removed by filtration. The filtrate is treated as in Example 1.

Results
DC mTFMA = 87.5%
YD n-allyl = 48.5%
YD diallyl = 4%
onium = 58.7%
selectivity = 92%

2nd Operation

The resin filtered off above is charged with:
4 mmol of m-TFMA
4 mmol of allyl chloride
2 ml of diisopropylethylamine.

The reaction, performed at 80° for 4 hours, is treated as above.

Results
DC MTFMA = 80%
YD N-allyl = 73.1%
YD diallyl = 6.2%
accounted for = 87.5%
selectivity = 92%

EXAMPLES 67 TO 69

Influence of the Reaction Time

The procedure is as in Example 1, charging:
0.64 g of m-trifluoromethylaniline (4 mmol)
0.3 g of allyl chloride (4 mmol)
2 ml of heptane
0.51 g of diisopropylethylamine (4 mmol)
0.4 mmol of tetraethylammonium bromide.

The reaction is performed at 80° for variable times.

TABLE 14

| Exp. | Time in min. | DC mTFMA | YD N-allyl | YD diallyl | Accounted for | Selectivity |
|------|--------------|----------|------------|------------|---------------|-------------|
| 67 | 240 | 77% | 84.8% | 9% | 94.8% | 90.3% |
| 68 | 140 | 65% | 89% | 6.3% | 96.6% | 93.4% |
| 69 | 60  | 47% | 86% | 3.6% | 95.7% | 96.5% |

EXAMPLES 70 TO 77

Influence of the Alkylating Agent a) Alkyl Halide

The procedure is as in Example 1, charging:
0.64 of m-trifluoromethylanilane (4 mmol)
4 mmol of an allyl halide
2 ml of heptane
0.51 g of diisopropylethylamine (4 mmol)
and, where appropriate, 0.4 mmol of allyltriethylammonium bromide.

The reaction is continued for four hours at 80° C.

TABLE 15

| Exp. | X⟍⟋ | ⟋⟍$NEt_3Br$ | DC mTFMA | YD N-allyl | YD diallyl | Selectivity |
|------|-----|-------------|----------|------------|------------|-------------|
| 70   | Cl⟍⟋ | yes | 71.4% | 82% | 6% | 93.2% |

TABLE 15-continued

| Exp. | X⤳ | ⤳NEt₃Br | DC mTFMA | YD N-allyl | YD diallyl | Selectivity |
|------|-----|---------|----------|------------|------------|-------------|
| 71   | Br⤳ | yes     | 83%      | 83.3%      | 10.8%      | 85.2        |

In the absence of onium ion, the degree of conversion is 7.5% for allyl chloride and 81.2% for allyl bromide. For 2 h 30 min at 25° C.

TABLE 16

| Exp. | X⤳ | ⤳NEt₃Br | DC mTFMA | YD N-allyl | YD diallyl | Selectivity |
|------|-----|---------|----------|------------|------------|-------------|
| 72   | Br⤳ | yes     | 85.7%    | 76.6%      | 11.6%      | 86.8%       |

In the absence of onium ion, the degree of conversion is 80%. For 1 h at 25° C.

TABLE 17

| Exp. | X⤳ | ⤳NEt₃Br | DC mTFMA | N-allyl YD | diallyl YD | Selectivity |
|------|-----|---------|----------|------------|------------|-------------|
| 73   | Br⤳ | yes     | 63%      | 84%        | 7%         | 92%         |

In the absence of onium ion, the degree of conversion is 20%.

b) Benzyl Halide

The procedure is as in Example 1, charging:
0.64 g of m-trifluoromethylaniline (4 mmol)
4 mmol of a benzyl halide
2 ml of heptane
0.51 g of diisopropylethylamine (4 mmol)
and, where appropriate, 0.4 mmol of an allyltriethylammonium bromide.
The reaction is allowed to continue at 80° C. for four hours.

TABLE 18

| Exp. | C₆H₅CH₂X   | ⁺⁻ NEt₃Br | DC mTFMA | YD N-benzyl | YD dibenzyl | Selectivity |
|------|------------|-----------|----------|-------------|-------------|-------------|
| 74   | C₆H₅CH₂Cl  | yes       | 95%      | 85%         | 15%         | 85%         |
| 75   | C₆H₅CH₂Br  | yes       | 85%      | 75%         | 25%         | 75%         |

In the absence of onium ion, the degree of conversion is 85% for benzyl chloride and 90% for benzyl bromide. At 25° C. for four hours.

TABLE 19

| Exp. | ⤳NEt₃Br⁺⁻ | DC mTFMA | YD N-benzyl | YD dibenzyl | Selectivity |
|------|-----------|----------|-------------|-------------|-------------|
| 76   | yes       | 43.5%    | 100%        | 0%          | 100%        |

In the absence of onium ion, the degree of conversion is 1%.

c) Isopropyl Bromide

The procedure as in Example 1, charging:
0.64 g of m-trifluoromethylaniline (4 mmol)
4 mmol of isopropyl bromide
2 ml of heptane
0.51 g of diisopropylethylamine (4 mmol)
and, where appropriate, 0.4 mmol of allyltriethylammonium bromide. The reaction is performed at 80° C. for four hours.

TABLE 20

| Exp. | ⤳NEt₃Br⁺⁻ | DC mTFMA | YD isopropyl | YD diisopropyl | Selectivity |
|------|-----------|----------|--------------|----------------|-------------|
| 77   | yes       | 25.7%    | 100%         | 0%             | 100%        |

In the absence of onium ion, there is no reaction.

EXAMPLES 78 TO 84

Influence of the Amine

The procedure as in Example 1, charging:
4 mmol of an amine
4 mmol of an allyl chloride
2 ml of heptane
4 mmol of diisopropylethylamine
0.4 mmol of allyltriethylammonium bromide.
The reaction is performed at 80° C. for four hours.

TABLE 21

| Exp. | X-aniline | pKa | ⌐NEt₃Br | DC X-aniline | YD N-allyl | YD diallyl |
|---|---|---|---|---|---|---|
| C 79 | NO₂ (p-nitroaniline) | 1 | no | 0% | | |
| 78 | | | yes | 43.2% | 100% | 0% |
| C 79 | CF₃ (m-trifluoromethylaniline) | 3.8 | no | 7.5% | 100% | 0% |
| 79 | | | yes | 77% | 82% | 6.5% |
| C 80 | Cl (p-chloroaniline) | 4.15 | no | 68.5 | 95% | 5% |
| 80 | | | yes | 85% | 81% | 17% |
| C 81 | (aniline) | 4.63 | no | 90.3% | 81.2% | 19.8% |
| 81 | | | yes | 92.4% | 75.3% | 24.7% |
| C 82 | OMe (p-anisidine) | 5.34 | no | 87% | 70% | 30% |
| 82 | | | yes | 90% | 60% | 40% |

The reaction was also performed for shorter periods.

TABLE 22

| Exp. | Aniline | Time | ⁺⁻NEt₃Br | DC aniline | YD N-allyl | YD diallyl |
|---|---|---|---|---|---|---|
| C 83 | NH₂ (aniline) | 1 h | no | 7.5% | 100% | 0% |
| 83 | | 1 h | yes | 67% | 95% | 5% |
| C 84 | | 4 h | no | 90.3% | 81.2% | 19.8% |
| 84 | | 4 h | yes | 92.4% | 75.3% | 24.7% | pKa = 4.63

Other embodiments of the invention will be apparent to one skilled in the art from a consideration of the specification, or with the practice of the disclosed invention.

We claim:

1. A process for the N-monoalkylation or N-monoallylation of an aniline, wherein the aniline and an alkylating or allylating agent, selected from the group consisting of alkyl chlorides, alkyl bromides, alkyl sulfates, allyl chlorides, allyl bromides and allyl sulfates, are brought into contact in an organic solvent in a homogeneous liquid phase in the presence of an onium ion and a stoichiometric amount of a non-quaternizable base.

2. The process as claimed in claim 1, wherein the allylating agent is allyl chloride.

3. The process as claimed in claim 1, wherein the said aniline possesses a pKa of less than 4.5.

4. The process as claimed in claim 3, wherein the aniline is chosen from haloanilines, perhaloalkylanilines, perhaloalkoxyanilines, perhaloalkylthionanilines and nitroanilines of formula (I):

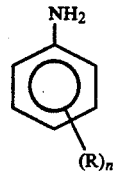

in which
R denotes
  a halogen;
  a group -AC$_n$X$_{2n+1}$ in which X denotes a halogen and
  A denotes a covalent bond or an oxygen or sulfur atom;
  an NO₂ group;
  n is equal to 1 or 2.

5. The process as claimed in claim 1, wherein the said onium ion is chosen from ammonium, phosphonium, sulfoxonium, sulfonium, carbonium, arsenium and oxonium ions.

6. The process as claimed in claim 5, wherein the onium ion is chosen from onium ions having a molecular weight of between 150 and 400.

7. The process as claimed in claim 6, wherein the onium ion is in the form of a supported onium compound.

8. The process as claimed in claim 1, wherein the said non-quaternizable base is an inorganic or organic base.

9. The process as claimed in claim 8, wherein the non-quaternizable base is an organic base chosen from sodium acetate or a tertiary amine bearing at least one branched alkyl group.

10. The process as claimed in claim 9, wherein the base is chosen from diisopropylallylamine, diisopropylethylamine or triisopropylamine.

11. The process as claimed in claim 10, wherein the base is diisopropylethylamine.

12. The process as claimed in claim 1, wherein the said onium ion can be formed within the reaction medium by the quaternization of a tertiary amine.

13. The process as claimed in claim 1, wherein the mole ratio of the alkylating or allylating agent to aniline is approximately 1:1.

14. The process as claimed in claim 1, wherein the mole ratio of the onium ion to the aniline is between 0.025 and 0.20.

15. The process as claimed in claim 1, wherein the solvent is chosen from aromatic and aliphatic hydrocarbon solvents, alcohols, polar aprotic solvents and non-quaternizable tertiary amines.

16. The process as claimed in claim 15, wherein the solvent chosen is heptane or diisopropylethylamine.

17. The process according to claim 6, wherein the onium compound is chosen from the ammoniums having a molecular weight of between 200 and 300.

18. The process according to claim 9, wherein said tertiary amine has at least two branched alkyl groups.

* * * * *